(12) United States Patent
Deterre et al.

(10) Patent No.: US 12,339,442 B2
(45) Date of Patent: Jun. 24, 2025

(54) DEVICE, PROJECTOR DEVICE AND METHOD FOR PROJECTING A LIGHT BEAM ONTO A RETINA OF A HUMAN EYE

(71) Applicant: La Science SAS, Paris (FR)

(72) Inventors: Martin Deterre, Paris (FR); Ralf Hornig, Bonn (DE); Emmanuel Simon, Paris (FR); Eric Abhamon, Paris (FR)

(73) Assignee: La Science SAS, Paris (FR)

( * ) Notice: Subject to any disclaimer, the term of this patent is extended or adjusted under 35 U.S.C. 154(b) by 658 days.

(21) Appl. No.: 17/593,276

(22) PCT Filed: Mar. 27, 2020

(86) PCT No.: PCT/EP2020/058874
§ 371 (c)(1),
(2) Date: Sep. 14, 2021

(87) PCT Pub. No.: WO2020/193797
PCT Pub. Date: Oct. 1, 2020

(65) Prior Publication Data
US 2022/0197022 A1 Jun. 23, 2022

(30) Foreign Application Priority Data
Mar. 28, 2019 (WO) .................. PCT/EP2019/057966

(51) Int. Cl.
*A61B 3/103* (2006.01)
*A61B 3/10* (2006.01)
(Continued)

(52) U.S. Cl.
CPC .......... *G02B 27/0081* (2013.01); *A61B 3/113* (2013.01); *G02B 26/0833* (2013.01);
(Continued)

(58) Field of Classification Search
CPC ......... A61B 3/102; A61B 3/02; A61B 3/1025; A61B 3/113; A61B 3/1015; A61B 3/103; A61B 3/1225; A61B 3/024; A61F 9/026
(Continued)

(56) References Cited

U.S. PATENT DOCUMENTS 5,703,637 A * 12/1997 Miyazaki ........... G02B 27/0172
348/E5.145
6,820,979 B1  11/2004 Stark et al.
(Continued)

FOREIGN PATENT DOCUMENTS

JP  2018068867 A  5/2018
WO  0133282  5/2001
(Continued)

*Primary Examiner* — Dawayne Pinkney
(74) *Attorney, Agent, or Firm* — Jeffrey Schox; Annabel Imbrie-Moore

(57) ABSTRACT

The present invention pertains to a projector device for projecting a light beam onto a retina of a human eye, comprising a projector for projecting a light beam from the exterior of a human eye through a pupil of the eye, wherein the projector is configured such that an exit pupil diameter of the light beam is set smaller than an eye pupil diameter of the eye, a corresponding method, and a device comprising such a projector device.

20 Claims, 13 Drawing Sheets

(51) Int. Cl.
    *A61B 3/113*     (2006.01)
    *A61B 3/12*     (2006.01)
    *G02B 26/08*     (2006.01)
    *G02B 27/00*     (2006.01)
    *G02C 11/00*     (2006.01)
    *G06F 3/01*     (2006.01)
    *H04N 9/31*     (2006.01)

(52) U.S. Cl.
    CPC .............. *G02C 11/10* (2013.01); *G06F 3/013* (2013.01); *H04N 9/3173* (2013.01)

(58) Field of Classification Search
    USPC ................ 351/211, 200, 205, 206, 209, 210, 351/221–223, 246
    See application file for complete search history.

(56) References Cited

U.S. PATENT DOCUMENTS

| | | | |
|---|---|---|---|
| 9,028,067 B1* | 5/2015 | Fleischman | G09B 21/008 351/209 |
| 10,175,490 B1 | 1/2019 | Serdarevic et al. | |
| 2008/0002262 A1 | 1/2008 | Chirieleison | |
| 2010/0097580 A1* | 4/2010 | Yamamoto | G02B 26/101 353/69 |
| 2010/0149073 A1 | 6/2010 | Chaum | |
| 2010/0152849 A1* | 6/2010 | Degenaar | A61F 9/08 623/6.63 |
| 2010/0204754 A1* | 8/2010 | Gross | A61N 1/36046 607/53 |
| 2011/0004272 A1 | 1/2011 | Seibel et al. | |
| 2013/0242262 A1* | 9/2013 | Lewis | H04L 5/0073 351/209 |
| 2013/0289668 A1 | 10/2013 | Nirenberg et al. | |
| 2015/0187141 A1* | 7/2015 | Bromer | G02B 26/0833 345/633 |
| 2017/0293147 A1* | 10/2017 | Tremblay | G02B 5/189 |
| 2018/0339170 A1* | 11/2018 | Luttrull | A61N 5/025 |
| 2019/0046798 A1* | 2/2019 | Kindt | A61F 9/0017 |
| 2019/0353897 A1* | 11/2019 | Suzuki | G02B 27/0081 |

FOREIGN PATENT DOCUMENTS

| | | |
|---|---|---|
| WO | 2013164665 | 11/2013 |
| WO | 2018/034783 | 2/2018 |

* cited by examiner

DEVICE, PROJECTOR DEVICE AND METHOD FOR PROJECTING A LIGHT BEAM ONTO A RETINA OF A HUMAN EYE

CROSS-REFERENCE TO RELATED APPLICATIONS

The present application is a 371 US National Stage Entry of PCT International Application No. PCT/EP2020/058874, filed Mar. 27, 2020, which claims priority to PCT International Application No. PCT/EP2019/057966, filed Mar. 28, 2019, the entire contents of which are incorporated by reference herein.

TECHNICAL FIELD

The invention relates to a projector device for projecting a light beam onto a retina of a human eye, a corresponding method, and a device for projecting a light beam onto a retina of a human eye comprising such a projector device.

TECHNOLOGICAL BACKGROUND

Retinal malfunction, in particular caused by degenerative retinal diseases, is a leading reason for visual impairment or even blindness.

For at least partially restoring a patient's visual function, it is known to modify a retinal area by making use of a retinal implant or in other words retinal prosthesis. In this regard, several different types of retinal implants are known, which are based on different working principles.

Retinal implants have in common that they are usually placed epiretinally or subretinally in the eye of the patient, such that they can replace in effect the damaged cells, such as photoreceptors. In this regard, information about a visual scene is captured with a camera and then transmitted to an electrode array implanted in the retina.

Among common retinal implants, implants are known which comprise skin-penetrating wires. These wires introduce risks of infection, scarring and leakage. Thus, more modern implants use different wireless techniques, for instance by delivering power and visual information through inductive coils. Furthermore, it is known to deliver power inductively and visual information optically through the pupil of the eye, or to deliver both visual information and power optically.

A particularly beneficial type of wireless information transfer to retinal implants is based on projecting stimulation patterns of infrared light into the eye. When the gaze direction is such that some part of the implants is illuminated by part of the pattern, the implant converts that part of the signal to electrical current that stimulates the retina accordingly.

The retinal implant is an array composed of stimulation electrodes or pixels. Each pixel has one or several photodiodes that capture the light delivered from a visual processor and converts it into electrical current for stimulation.

Several implant arrays can be placed in the subretinal space, typically in or close to the foveal area.

For projecting light or a light beam into a human eye, it is known to use a projector device, such as augmented reality goggles. A projector of the projector device projects the light beam onto the human eye, wherein the light beam is far broader than the pupil of the human eye. This light beam is designed on purpose broader than the pupil of the human eye to allow an imprecision of the placement of the projector with respect to the human eye while still perceiving part of the light beam and further to allow eye movements to a certain extent. That is, only a part of the light beam to be transmitted is led into the eye through its eye pupil and towards the retina with an unknown irradiance as the pupil size of the eye may largely vary.

Retinal implants based on projection of infrared light, in fact, require specific irradiance for correct operation. Thus, ordinary augmented reality goggles are unsuitable in combination with such designed retinal implants.

The aforementioned projector devices can also be used in optogenetic applications to modify or improve a targeted retinal area in the eye, such as reactivating the photosensibility of the targeted area of the retina. Optogenetics refers to the combination of genetics and optics to control well-defined events within specific cells of living tissue. Optogenetics consists in (i) genetically modifying target cells in order to render them sensitive to light by the expression of exogenous photoreactive proteins in cellular membrane and (ii) providing illuminating device able to provide light to said photoreactive proteins. Activation of the exogenous photoreactive proteins in cellular membrane requires specific irradiance of the light.

As the light beam arriving onto the retina comprises an unknown irradiance, it is difficult to adjust the irradiance to an appropriate level. Thus, damages on the targeted area or an insufficient effect on the targeted area may result due to too high or too low irradiance, respectively.

SUMMARY OF THE INVENTION

It is an object of the present invention to provide an improved projector device for projecting a light beam onto a retina of a human eye, as well as providing a corresponding method for projecting a light beam onto a retina of a human eye.

According to a first aspect, a projector device for projecting a light beam onto a retina or retinal area, more specifically modified retinal area, of a human eye is suggested, which comprises a projector for projecting a light beam from the exterior of a human eye through the pupil of the eye. The projector device is further configured such that an exit pupil diameter of the light beam is set smaller than an eye pupil diameter of the eye. According to preferred embodiment, the projector device is configured such that there is only one light beam and one exit pupil diameter of the light beam set smaller than an eye pupil diameter of the eye.

According to the present invention, retinal area of the human eye that has been modified to restore photosensitive behavior through implantation of a retinal prosthesis or modification by optogenetics will also be referred to as "modified retinal area".

By configuration of the projector device such that the exit pupil diameter of the light beam is set smaller than an eye pupil diameter of the eye, it is possible that the whole light beam always enters the eye through the eye pupil for a suitable range of eye pupil sizes and gaze directions. Hence, the modified retinal area (e.g. the retinal implant) can be illuminated with the light beam with a predetermined or (pre-)specified irradiance, as it may be ensured that no radiant power is lost at the iris of the human eye. Furthermore, there may be no radiance variation on the retina, and hence on modified retinal area, for example on the retinal implant.

According to another preferred embodiment, the projector is configured such that the exit pupil diameter is equal to or smaller than 3 mm, preferably equal to or smaller than 2 mm, more preferably equal to or smaller than 1 mm, particularly preferably equal to or smaller than 0.5 mm, and particularly preferably, the exit pupil diameter is set to 1 mm, 0.75 mm, 0.5 mm, or 0.25 mm.

As the diameter of the human eye pupil is usually bigger than 3 mm, and usually varies between 3 mm and 8 mm, by setting the exit pupil diameter to equal to or smaller than 3 mm, it may be achieved that the whole light beam enters through the eye pupil in nominal conditions, and thus there is no irradiance variation on the retina due to loss of power in blocked parts of the light beam.

According to a further preferred embodiment, the projector device may comprise a sensor unit for monitoring the eye pupil diameter of the eye the light beam is projected to and/or for monitoring an ambient light intensity, wherein the sensor unit preferably comprises a camera and/or a photo-detector, wherein the projector comprises an adjustment unit for adjusting the exit pupil diameter based on the monitored value of the eye pupil diameter and/or of the ambient light intensity. Thereby, it can be ensured that the exit pupil of the light beam is always adjusted or set equal to or smaller than the present eye pupil diameter, such that substantially the whole light beam can enter the eye and reach the retina, more particularly the modified retinal area or the retinal implant.

Alternatively or in addition, the projector may be adapted for adjusting the irradiance of the output beam based on the monitored value of the eye pupil diameter and/or of the ambient light intensity.

According to a further preferred exemplary embodiment, an adjustment unit may comprise a preferably exchangeable dioptric correction wedge.

According to a further preferred embodiment, the projector is configured:

such that an exit pupil distance of the light beam emitted by the projector is adjustable in the range from 5 mm to 50 mm, preferably from 10 mm to 30 mm; and/or wherein preferably, an exit pupil plane defined by the exit pupil of the light beam is aligned to an eye pupil plane defined by the eye pupil; and/or wherein preferably a maximum distance between the exit pupil plane and the eye pupil plane is ±5 mm, preferably ±3 mm, more preferably ±2 mm, even more preferably ±1 mm, and particularly preferably 0.5 mm.

Thereby, it can be ensured that when the projector device is correctly positioned in front of the human eye, the exit pupil distance can be adjusted to the eye relief, that is the distance between the projector and the eye, in particular a plane defined by the eye pupil. Preferably, adjustment of the exit pupil distance is performed by an adjustment unit of the projector device or the projector itself, respectively.

In particular, when according to another preferred embodiment, both the exit pupil diameter of the light beam and the exit pupil distance is adjusted to the eye pupil diameter and to the eye relief, respectively, it can be ensured that the diameter of the light beam at the eye pupil plane is smaller than the diameter of the eye pupil. Hence, thereby it may be achieved that always the whole light beam enters the eye reaches the retina, more particularly the modified retinal area, and potentially the retinal implant.

According to yet another preferred embodiment, the projector device is configured to control an irradiance of the light beam. Thereby, it can be ensured that the retina, more particularly the modified retinal area, and specifically retinal implant is always irradiated with the correct irradiance.

According to another preferred embodiment, the projector device comprises an alignment device for aligning a central axis of the light beam with a center of the eye pupil, wherein preferably a maximum deviation between the central axis of the light beam and the center of the eye pupil is equal to or less than 1 mm. Hence, by means of the alignment device, loss of power on the iris due to a misalignment of the light beam with respect to the eye pupil can be avoided.

Preferably, the alignment device is configured for aligning to the central axis of the light beam with a viewing axis, being defined as the axis passing by the center of the eye pupil and a center of an implant of the eye, wherein preferably a maximum deviation between the central axis of the light beam and the viewing axis is equal to or less than 1°. Hence, by means of the alignment device, loss of power on the iris and particularly on the retina, more particularly the modified retinal area, and specifically the retinal implant due to a misalignment of the light beam with respect to the eye pupil can be avoided.

With other words, when simultaneously, according to a particularly preferred embodiment, the exit pupil diameter of the light beam is set smaller than an eye pupil diameter of the eye as described above, the exit pupil plane defined by the exit pupil of the light beam is aligned to the eye pupil plane defined by the eye pupil as described above, and the central axis of the light beam is aligned with the center of the eye pupil preferably the viewing axis, it is ensured that the light beam enters the eye pupil in its entirety and reaches the retina, more particularly the modified retinal area, and specifically the retinal implant. Hence, according to this exemplary embodiment, the irradiance onto the retina, more particularly the modified retinal area, and specifically the retinal implant may always be known and/or predetermined.

According to another preferred embodiment, the alignment device is motorized and dynamic and coupled with an eye observation module, preferably an eye position sensor, allowing direction of the projection to follow the eye direction. In that embodiment, the eye observation module, which can be an eye tracker device which monitors the eye position and angle, provides the alignment requirement to the alignment device, and the alignment device automatically adjusts the position and angle of the projection beam, for instance with micromirrors or piezoelectric micro-motors, to ensure a correct alignment being done automatically and regularly. With other words, the alignment device may include a motorized unit configured to couple the direction of projection with an eye direction as monitored by an eye observation module, preferably an eye tracking device, wherein the eye observation module preferably is embedded in the projection device.

In a further preferred embodiment, the projector device comprises a fastening section for fastening the projector device onto a frame, preferably a spectacles frame, wherein the alignment device is configured such that a position and/or an orientation of the projector can be adjusted with respect to the fastening section. Hence, alignment of the light beam with respect to the eye pupil may be achieved simply by adjusting the position of the projector with respect to the fastening section.

For providing the above-mentioned adjustability, according to a further preferred embodiment, the alignment device is formed such that the projector can be moved relative to the fastening section in a plurality of movement directions, particularly preferably in five movement directions.

Preferably, the alignment device is formed such that at least one of the movement directions is a longitudinal direction, wherein preferably two movement directions are longitudinal directions, and particularly preferably three movement directions are longitudinal directions.

In this regard, preferably each longitudinal direction is oriented substantially orthogonal to at least one other longitudinal direction, wherein preferably each of the longitudinal directions is oriented orthogonal to all other longitudinal directions.

It has been shown that adjustment as described above can be achieved in a particularly beneficial way, when according to a preferred embodiment, one movement direction corresponds to a longitudinal axis of a human head, and/or one movement direction corresponds to a transversal axis of a human head, and/or one movement direction corresponds to a sagittal axis of a human head.

Accordingly, when a movement direction corresponds to a longitudinal axis of the human head, and another movement direction corresponds to the transversal axis of the human body, the direction of the light beam can be adjusted, such that the central axis of the light beam is projected onto the center of the eye pupil.

Furthermore, when a movement direction corresponds to the sagittal axis for human head, the eye relief, hence the distance between the projector or a surface of the projector facing towards the eye, and the eye pupil can be adjusted.

According to another preferred embodiment, the alignment device is formed such that at least one of the movement directions is a direction of rotation, preferably two movement directions are directions of rotation. Thereby, misalignments of the light beam with respect to an axis defined by the eye pupil and the retina, more particularly the modified retinal area, and specifically the retinal implant can be compensated.

Thereby, preferably one direction of rotation is oriented such that a pantoscopic angle of the projector with respect to the eye can be adjusted, and/or one direction of rotation is oriented such that a wrap angle of the projector with respect to the eye can be adjusted.

When according to yet another preferred embodiment the alignment device comprises at least one kinematic pair, preferably a plurality of kinematic pairs, wherein preferably at least one kinematic pair is a prismatic joint and/or wherein preferably at least one kinematic pair is a rotating joint, and/or wherein the alignment device comprises at least one locking unit, preferably a locking screw, for locking of at least one movement direction, adjustment and/or alignment of the projector and/or the light beam with respect to the fastening section and/or an eye pupil of a human eye may be provided in a robust and simple way.

According to yet another preferred embodiment, the projector device further comprises a camera for capturing patterns of interest in front of the projector device, wherein a content of the light beam is based on the captured pattern of interest, wherein preferably a main axis of the camera is aligned with a main axis of the light beam, preferably concentrically aligned, wherein preferably the camera and the projector are arranged in line facing opposite sides of the device.

Thereby, it can be ensured that when a person equipped with the projector device is looking straight ahead, the person may see exactly what is straight ahead of him. With other words, thereby, it may be easier for the person to focus on a point of interest and moreover to orient in space.

According to yet another preferred embodiment, the projector device comprises a micromirror array, preferably a digital micromirror device which is per se known, wherein the light beam is based on patterning light directed onto the micromirror array, preferably light emitted by a laser, laser diode and/or an LED, preferably an LED-Matrix. With other words, the micromirrors of the micromirror array each reflect a part of the incident light beam, thereby generating a reflected, patterned exit light beam.

Preferably, light, preferably comprising a wavelength in the near infrared field, is lead into a total internal reflection (TIR) prism, the light then hits an active area of the micromirror array where the micromirrors select what part of the micromirror array disk is reflected toward the eye and thus creating a pattern, the patterned light passes through the TIR prism again, and the patterned light goes through a final lens and thereby exits the projector.

Preferably, the light beam is based on incoherent light such that diffraction effects or interference patterns can be neglected.

According to another preferred embodiment, the light beam is based on coherent light. Thereby it is possible that the micromirror array causes diffraction or interference patterns of the light beam.

According to yet another preferred embodiment, the projector device is adapted such that an incident angle of the coherent light and a pitch of the micromirrors of the micromirror array are configured such that a distance between intensity maxima of adjacent orders of diffraction, preferably of the two most powerful orders of diffraction, of an output beam is equal to or greater than 7 mm, preferably equal to or greater than 8 mm, more preferably equal to or greater than 10 mm. Thereby, it can be ensured that only one intensity maxima enters the eye pupil, which normally extends between 3 to 7 mm in diameter. Hence, the irradiance on the internal implant can reliably be (pre-)determined.

Alternatively, the projector device is adapted such that an incident angle of the coherent light and a pitch of the micromirrors of the micromirror array are configured such that the majority of the power of the light beam goes into a single order of diffraction. Preferably, 70% to 95%, more preferably 80% to 95%, more preferably 90% of the light is directed into one order of diffraction. Hence, other orders may become negligible in terms of power, and therefore whether these orders also enter the pupil or not is not significant, as they do not significantly affect the irradiance on the retina, more particularly the modified retinal area, and specifically the retinal implant.

When according to yet another preferred embodiment, the projector device comprises a preferably detachable eye observation module for observing at least a part of the retina, preferably a part of the retina at which the light beam is targeted (for example the modified retinal area, and specifically the retinal implant) and/or for observation of the eye pupil, wherein preferably, the eye observation module and the light beam comprise the coincident optical axes, the eye observation module may be attached to the projector device for adjusting, aligning and/or centering the light beam projected by the projector device into a patient's eye pupil and onto a retina, more particularly the modified retinal area, and specifically the retinal implant of the patients, when the patient wearing a device comprising a projector device according to one of the above-mentioned embodiments. Preferably, adjustment of the light beam is performed by trained medical staff. After adjustment, the eye observation module may be detached as it is no longer needed. In addition or as an alternative, the eye observation module may be used for observing the eye pupil and/or for observation of the projected pattern on the retina.

According to another preferred embodiment, the eye observation module is adapted to observe the retinal implant implanted in the retina. This allows to further adjust the light beam projected by the projector device with respect to the retinal implant.

Preferably, the projector device further comprises a distance sensor for determining an eye relief, that is a distance between the projector device and the eye pupil.

According to another preferred embodiment, the projector device is adapted to transmit one or more test patterns which can be used to adjust the alignment of the beam emitted by the projector device and the eye pupil and/or the retinal implant.

According to another aspect, a device for projecting a light beam into a human eye is suggested, which comprises a frame and a projector device according to any one of the preceding embodiments, wherein the projector device is fixed to the frame, preferably by means of its fastening section.

The effects and advantages described with regard to the projector device may analogously be achieved by the device for projecting a light beam into a human eye.

According to a preferred embodiment, the frame is a spectacles frame, and/or wherein the frame comprises a headband, and/or wherein the frame comprises a heading, and/or the frame comprises ear stoppers.

According to another preferred embodiment, the device comprises a lens held by the frame, wherein preferably, the lens is arranged at the frame to cover the eye when the device is worn. The lens preferably is shaded, preferably tinted. By providing the shaded lens, the eye pupil diameter may naturally be enlarged as less ambient light falls into the eye pupil. Hence, alignment of the central axis to the center or the viewing axis, respectively, may be facilitated.

According to another preferred embodiment, the frame is adapted to allow for at least some of the above alignments, preferably the frame comprises a hinge arranged between a front frame and a temple of the frame. By means of hinge, a temple is pivotable relative to the front frame.

Alternatively or in addition, on at least one temple, a displaceable ear pad may be arranged which can be displaced along the temple.

For supporting front frame on the patient's nose, one or more adjustable nose pads may preferably be provided.

By means of the aforementioned parts, the frame may be adjusted to the patient's individual head form prior for at least supporting adjustment of the light beam with respect to the eye pupil. In particular, the ear pads may be moved forward or backward on the temples relatively to each other to adjust the wrap angle of the front of the frame and hence of the projector.

According to yet another aspect of the invention, a method for projecting an image onto a retina, more particularly the modified retinal area, and specifically the retinal implant of a human eye or a method for operating a projector device as described herein for projecting an image is suggested, comprising projecting a light beam from the exterior of a human eye towards the pupil of the eye, wherein an exit pupil diameter of the light beam is set smaller than an eye pupil diameter of the eye.

The effects and advantages described with regard to the projector device above may also be anonymously achieved by the method.

According to another preferred embodiment, the method further comprises the step of aligning a central axis of the light beam to a center of the eye pupil, wherein preferably a maximum deviation between the central axis of the light beam and the center of the eye pupil is equal to or less than 1 mm, wherein preferably, the central axis of the light beam is aligned with a viewing axis, being defined as the axis passing by the center of the eye pupil and a center of an implant of the eye, wherein preferably a maximum deviation between the central axis of the light beam and the viewing axis is equal to or less than 1°.

According to another preferred embodiment, the exit pupil diameter is set equal to or smaller than 3 mm, preferably equal to or smaller than 2 mm, more preferably equal to or smaller than 1 mm, particularly preferably equal to or smaller than 0.5 mm, and particularly preferably the exit pupil diameter is set to 1 mm, 0.75 mm, 0.5 mm, or 0.25 mm.

According to yet another preferred embodiment, an exit pupil plane defined by the exit pupil of the light beam is aligned to an eye pupil plane defined by the eye pupil, wherein preferably a maximum distance between the exit pupil plane and the eye pupil plane is ±5 mm, preferably ±3 mm, more preferably ±2, even more preferably ±1, and particularly preferably 0.5 mm.

According to yet another preferred embodiment, an exit pupil distance of the light beam is adjustable in the range from 5 mm to 50 mm, preferably 10 mm to 30 mm.

According to another preferred embodiment, the exit pupil distance is adjusted to a distance between the projector and the eye pupil.

According to another preferred embodiment, the method further comprises the steps of monitoring the eye pupil diameter of the eye the light beam is projected to and/or monitoring an ambient light intensity, and adjusting the exit pupil diameter based on the monitored value of the eye pupil diameter and/or the ambient light intensity.

According to yet another preferred embodiment, the light beam is based on patterning of coherent light, preferably light emitted by a laser, a laser diode, directed onto a micromirror array, wherein an incident angle of the coherent light and a pitch of the micromirrors are configured such that a distance between intensity maxima of adjacent orders of diffraction, preferably of the two most powerful orders of diffraction, of an output beam at the exit pupil plane is equal to or greater than 7 mm, preferably equal to or greater than 8 mm, more preferably equal to or greater than 10 mm.

Alternatively, the light beam may be based on patterning of incoherent light, preferably light emitted by an LED, to substantially avoid effects of interferences.

BRIEF DESCRIPTION OF THE DRAWINGS

The present disclosure will be more readily appreciated by reference to the following detailed description when being considered in connection with the accompanying drawings in which.

DETAILED DESCRIPTION OF PREFERRED EMBODIMENTS

Figure 1:
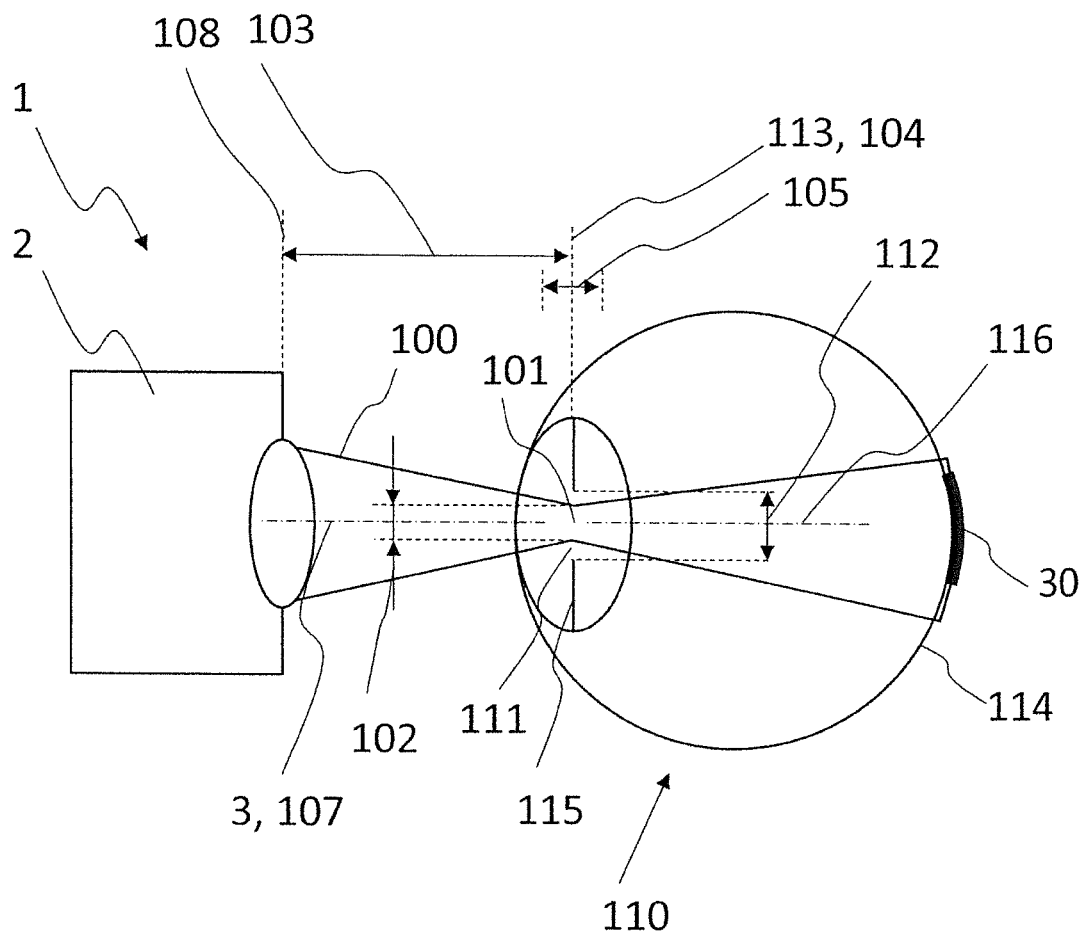
FIG. 1 is a schematic side view of a projector device for projecting a light beam onto a retina of a human eye according to a first embodiment.

In the following, the invention will be explained in more detail with reference to the accompanying figures. In the Figures, like elements are denoted by identical reference numerals and repeated description thereof may be omitted in order to avoid redundancies.

FIG. 1 is a schematic side view of a projector device 1 for projecting a light beam 100 onto a retina 114 of a human eye 110 according to a first embodiment. In this exemplary embodiment, the light beam 100 comprises a wavelength in the near infrared field (NIR).

The projector device 1 comprises a projector 2 for projecting a light beam 100 from the exterior of the human eye 110 through a pupil 111 of the eye 110. The projector 2 is configured such that an exit pupil diameter 102 of an exit pupil 101 of the light beam 100 is set smaller than an eye pupil diameter 112 of the eye.

Thereby, it is ensured that substantially the whole energy of the light beam 100 enters the eye 110 through the eye pupil 111. Hence, the retinal implant 30 implanted in the retina 114 is irradiated with substantially the whole irradiance of the light beam 100. With other words, the irradiance on the retinal implant 30 is known. Also, variation of the irradiance on the retinal implant 30 can be avoided. Hence, by controlling the irradiance of the light beam 100 at the projector device 1, the irradiance on the targeted area of the retina is known and can be controlled. Accordingly, proper operation of the retinal implant 30 and/or proper functioning of optogenetic applications can be ensured.

The irradiance on the retinal implant 30 is crucial for functioning of the retinal implant 30.

For ensuring that the entire light beam 100 having its exit pupil diameter 102 set smaller than the eye pupil 111 enters the eye pupil 111, the central axis central axis 107 of the light beam 100 is aligned with the center 116 of the eye pupil 111. In this regard, it has been shown that a maximum deviation between the central axis 107 and the center 116 equal to or smaller than 1 mm provides adequate accuracy.

In addition, an exit pupil plane 104 defined by the exit pupil 101 of the light beam 100 is aligned to an eye pupil plane 113 defined by the eye pupil 111. Thereby, it can be ensured that the diameter of the light beam 100 is smaller than the eye pupil diameter 112 at the eye pupil plane 113. For doing so, the exit pupil distance 103 extending between the projector exits plane 108 and the exit pupil plane 104 is adjusted to the distance between the projector 108 and the eye pupil 111, thus the eye relief.

It has been shown that when the alignment of the exit pupil plane 104 to the eye pupil plane 113 is within a tolerance having a maximum distance of ±5 mm, preferably ±3 mm, more preferably ±2, even more preferably ±1, and particularly preferably 0.5 mm, adequate alignment is achieved.

The above described alignment of central axis 107 and center 116 as well as exit pupil plane 104 and eye pupil plane 113 is provided by means of an alignment device (not shown in FIG. 1) of the projector device 1, which is described in detail below.

Setting the exit pupil diameter 102 smaller than the eye pupil diameter 112 may be provided by setting the exit pupil diameter 102 to a fixed value which is smaller than an estimated minimum eye pupil diameter 112. It has been shown that when the exit pupil diameter 102 is set to a value equal to or smaller than 3 mm, preferably equal to or smaller than 2 mm, more preferably equal to or smaller than 1 mm, particularly preferably equal to or smaller than 0.5 mm, it can be ensured that the eye pupil diameter 112 is always greater than the exit pupil diameter 102. Advantageous values for the exit pupil diameter 102 are 1 mm, 0.75 mm, 0.5 mm, or 0.25 mm.

Alternatively or in addition, the projector 2 may comprise an adjustment unit (not shown) for adjusting the exit pupil diameter 102 based on a monitored value of the eye pupil diameter and/or of the ambient light intensity surrounding the projector device 1.

In this regard, the projector device 1 may comprise a sensor unit configured for monitoring the eye pupil diameter 112. Hence, the adjustment unit can set the exit pupil diameter 102 smaller than the measured eye pupil diameter 112. In this regard, it has been shown advantageous when the sensor unit comprises a camera for monitoring the eye pupil 111.

Alternatively or in addition, the sensor unit may be configured for monitoring the ambient light intensity. As the eye pupil diameter 112 is substantially depending on the ambient light intensity, with other words, as the eye pupil diameter 112 is a function of the ambient light intensity, the sensor unit may determine the eye pupil diameter 112 based on the measured light intensity, e.g. by comparing them value of the measured light intensity with values stored in a lookup table. In this regard, it has been shown advantageous when the sensor unit comprises a photodetector.

It may be particularly comfortable for a person who is equipped with the projector device 1 when the eye relief between the projector 2, hence the projector exit plane 108, and the eye pupil 111 is arranged in a distance between 5 to 50 mm, preferably 10 mm to 30 mm. Thus, the projector 2 is optionally configured such that an exit pupil distance 103 of the light beam 100 emitted by the projector 2 is adjustable in the range from 5 mm to 50 mm, preferably 10 mm-30 mm, preferably by means of the adjustment unit.

The alignment device 4 optionally is configured for aligning the central axis 107 of the light beam 100 with a viewing axis, being defined as the axis passing by the center 116 of the eye pupil and a center of an implant of the eye 110, wherein preferably a maximum deviation between the central axis 107 of the light beam 100 and the viewing axis is equal to or less than 10.

Figure 2:
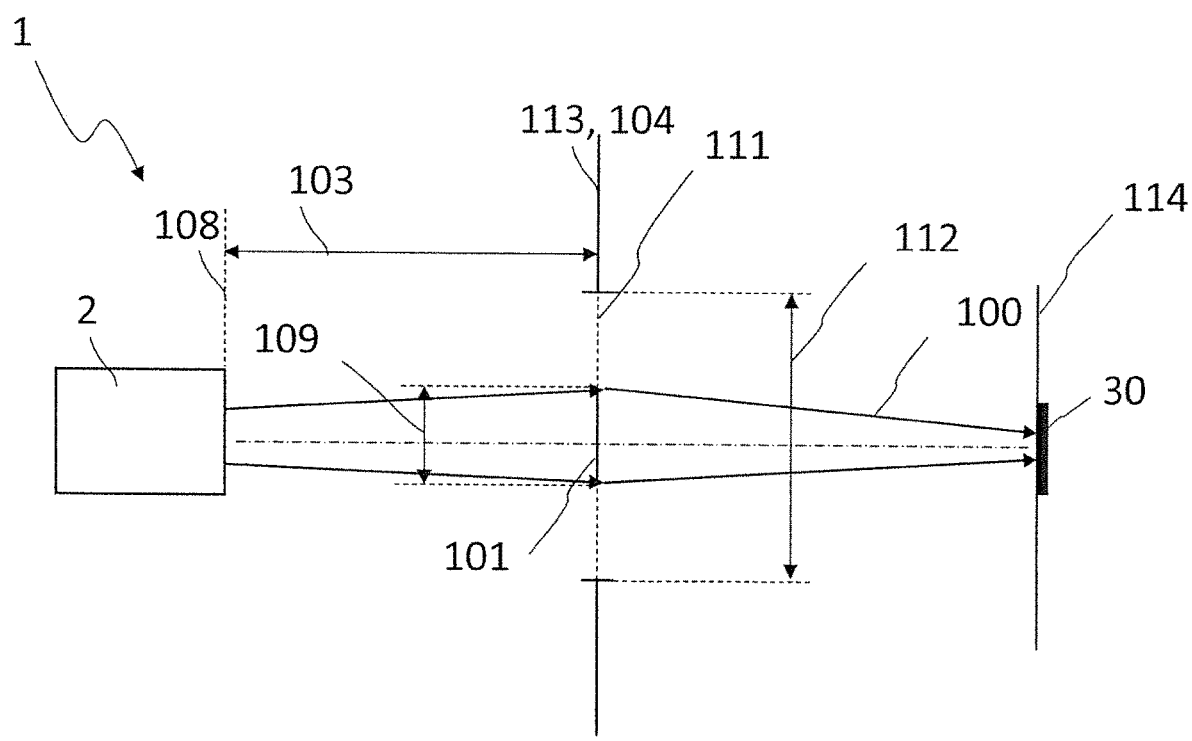
FIG. 2 is a schematic side view of a projector device for projecting a light beam onto a retina of a human eye according to a second embodiment.

FIG. 2 is a schematic side view of a projector device 1 for projecting a light beam 100 onto a retina of a human eye 110 according to a second embodiment. This embodiment substantially corresponds to the embodiment shown in FIG. 1. Again, the output beam diameter 109 which is herein disclosed to be seen corresponding to the exit pupil diameter 102 at the eye pupil location is set smaller than the eye pupil diameter 112. Hence, substantially the whole light energy of the light beam 100 arrive at the retinal implant 30. That is, again, the irradiance at the retinal implant 30 is known and can be controlled at the projector device 1.

Figure 3A:
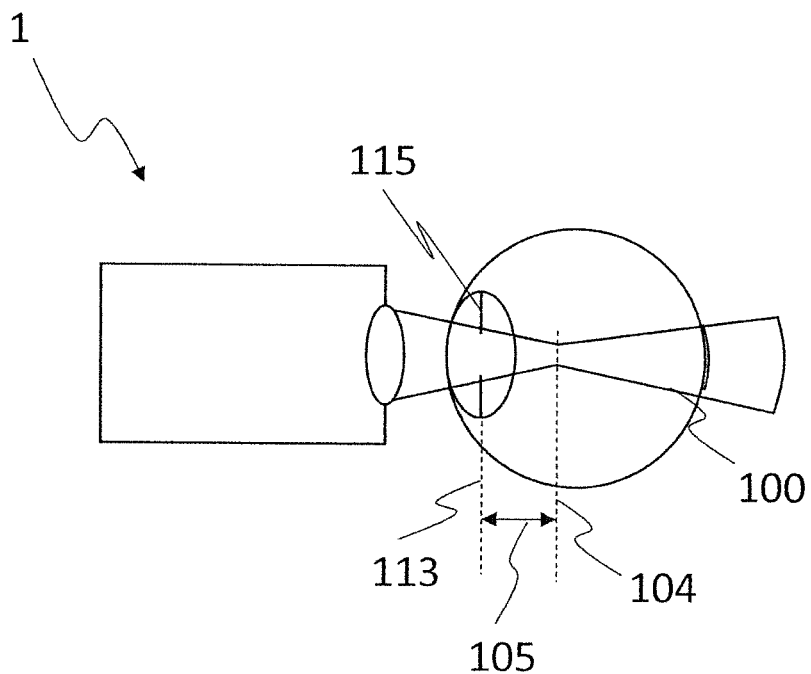
FIGS. 3a and 3b schematically show side views of a projector device having misaligned light beams.
Figure 3B:
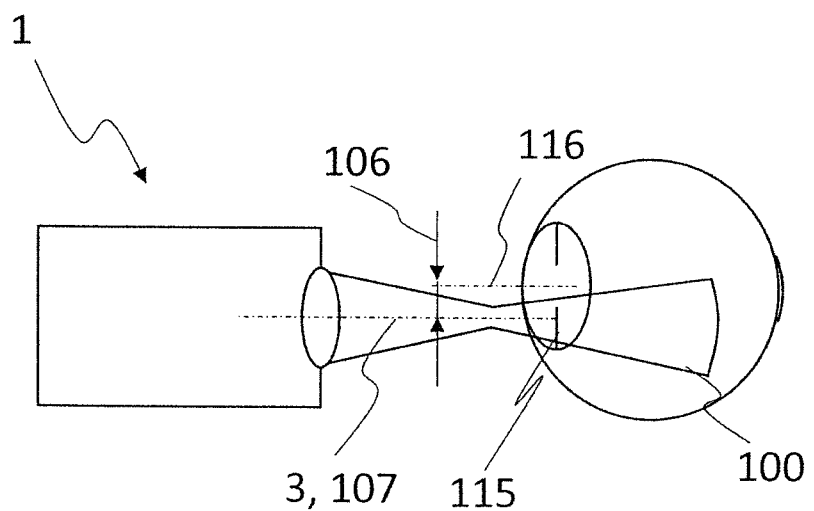

FIGS. 3a and 3b schematically show side views of a projector device 1 according to FIG. 1 having misaligned light beams 100.

By these figures it can be seen that the alignment of the light beam, hence the exit pupil 101, with respect to the eye pupil 111 is from significant importance.

In FIG. 3A, the exit pupil plane 104 is misaligned to the eye pupil plane 113 with a distance 105 greater than the above described tolerance. Hence, although the exit pupil diameter 102 is set smaller than the eye pupil diameter 112, the light beam 100 is particularly blocked by the iris 115.

In FIG. 3B, in turn, the central axis 107 of the light beam 100 is misaligned to the center 116 of the eye pupil 112 by a deviation 106 greater than the above described maximum deviation 106. As can be seen, the light beam 100 is also partially blocked by the iris 115.

Hence, only when the alignment is described above with regard to FIG. 1 is performed, that is the exit pupil distance 103 is correctly set or adjusted, and the main axis 3 of the projector 2, which corresponds to the central axis 107 of the light beam 100 is correctly set or adjusted, it can be ensured that the light beam 100 having an exit pupil diameter 102 smaller than the eye pupil diameter 112 in total enters the eye 110.

Figure 4A:
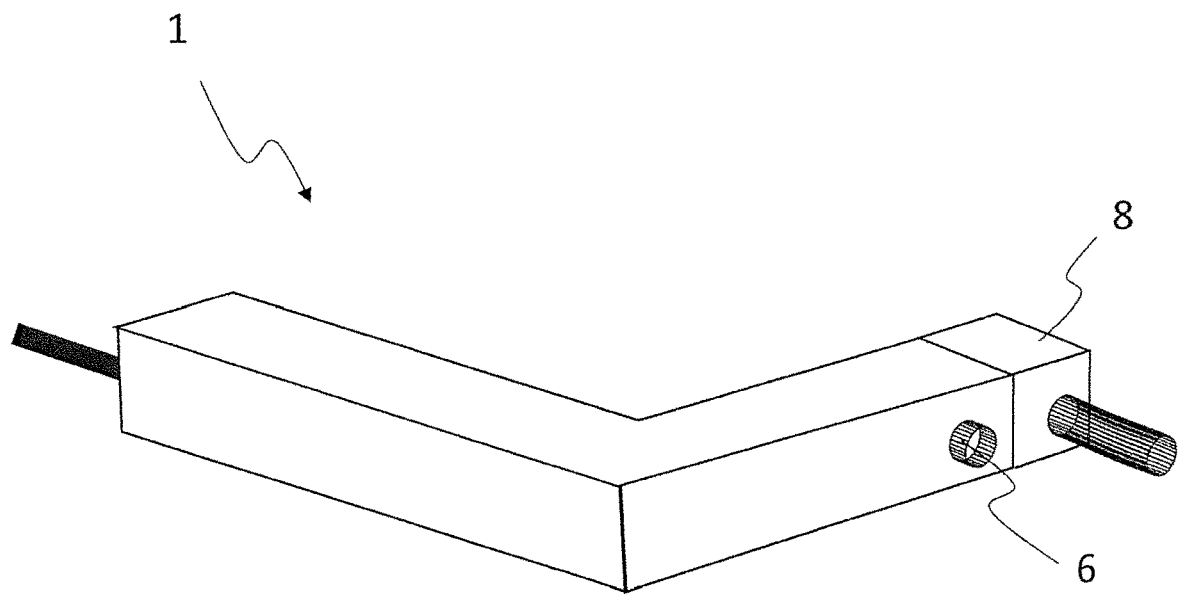
FIGS. 4A and 4B are schematic side views of projector devices for projecting a light beam onto a retina of a human eye according to preferred embodiments.

FIG. 4A is a schematic perspective side view of a projector device 1 for projecting a light beam onto a retina of a human eye according to another embodiment. The projector device 1 substantially corresponds to the projector device 1 described with regard to FIG. 1. As can be seen in FIG. 4A, in this exemplary embodiment, the projector device 1 comprises a camera 6 for capturing patterns of interest in front of the projector device 1. The captured pattern of interest captured by the camera 6 provides basis for the content of the light beam 100 which is projected into the human eye 110 and onto the retinal implant 30.

Moreover, the projector device 1 comprises an optional preferably detachable eye observation module 8 for observing at least a part of the retina 114 and/or the iris 115, preferably a part of the retina 114 at which the light beam 100 is targeted. Preferably, the content captured by the eye observation module is led to a video screen (not shown), wherein preferably the video screen is aligned with the light beam 100 and the implant 30. When the iris 115 is observed, it is possible to observe the alignment of the output beam to the eye pupil 111 for monitoring whether further adjustment needs to be performed.

Thereby preferably the eye observation module 8 is configured such that the retinal implant 30 on the back of the eye 110 and also the projected beam 100 on the retina 114 can be monitored and thus shown on the video screen.

In a further preferred embodiment, the eye observation module 8 comprises an optical path that can be combined with the optical path of the projection, for instance through dielectric mirrors and/or beam splitters, hence permitting the direct visualization of the projected beam on the eye observation camera 6. Preferably, the camera 6 is positioned on one of the sides of the module, and is optically connected, preferably via lenses, and/or mirrors and/or beam splitters, to the optical path of the projection, that is the output beam 22.

Simple alignment of the eye pupil 111 and the light beam 100 may be achieved and/or may be controlled when adjusting the light beam 100, hence the projector device 1 with respect to the human eye 110. Moreover, the above may be helpful for training a patient equipped with the projector device 1.

Figure 4B:
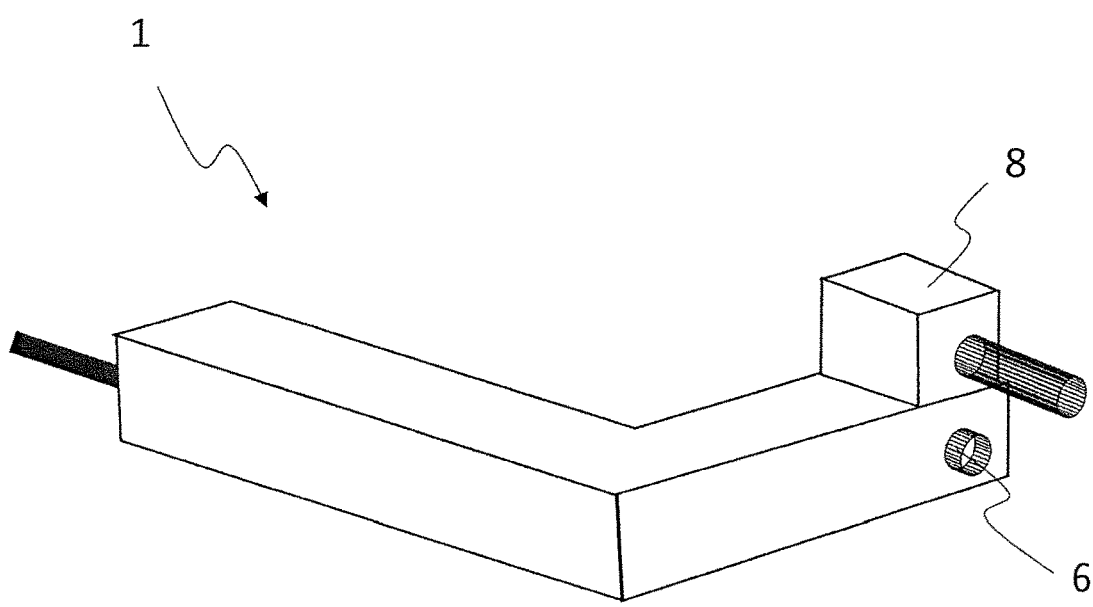

FIG. 4B shows a schematic perspective side view of a projector device 1 for projecting a light beam onto a retina of a human eye according to another embodiment. The projector device 1 substantially corresponds to the projector device shown in FIG. 4A, wherein the eye observation module 8 is arranged on another location at the projector device 1.

Figure 5:
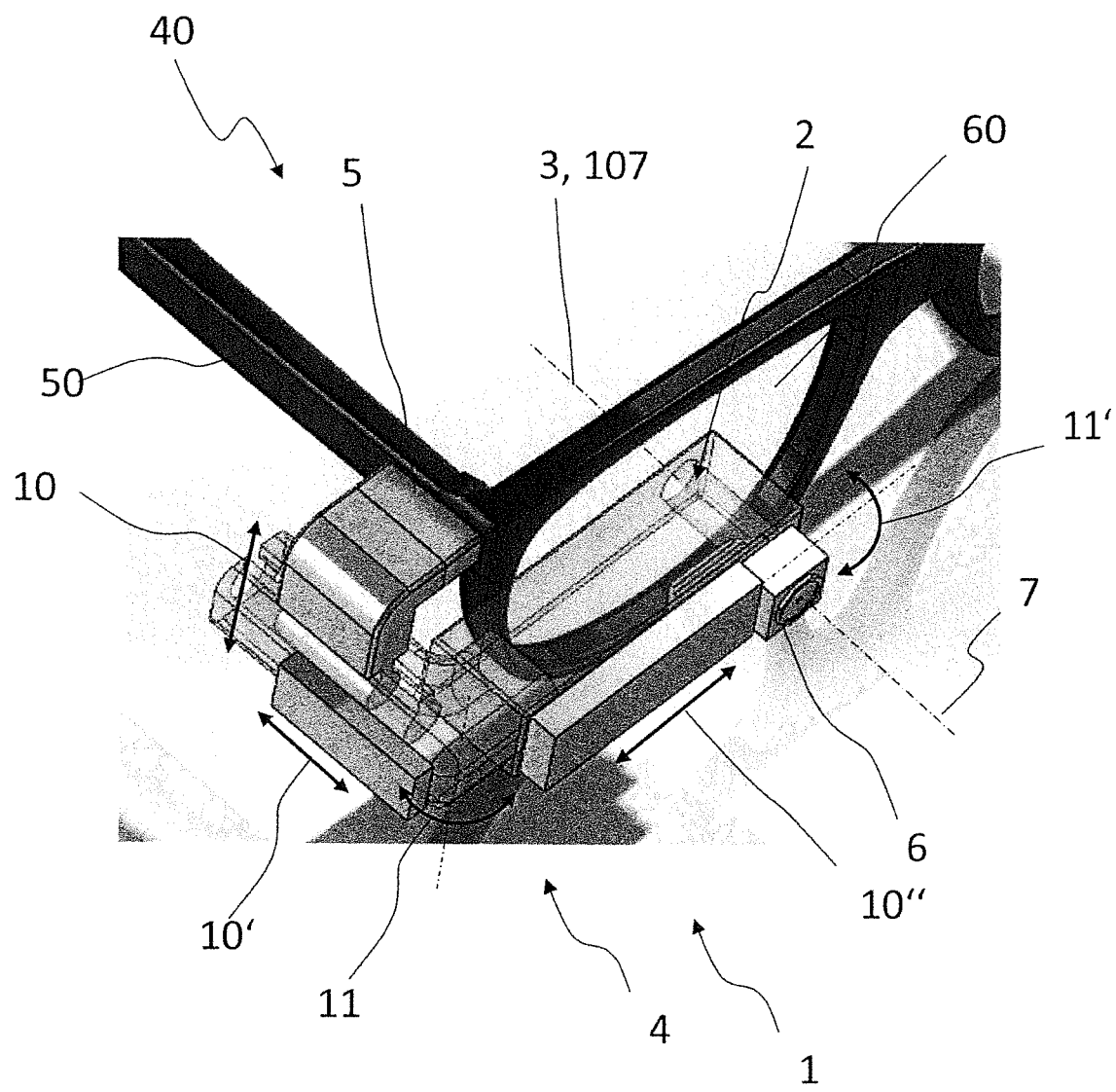
FIG. 5 is a schematic side view of a device for projecting a light beam onto a retina of a human eye according to an exemplary embodiment.

FIG. 5 is a schematic side view of a device 40 for projecting a light beam onto a retina of a human eye according to an exemplary embodiment.

The device 40 comprises a frame 50 which in this embodiment is implemented in form of a spectacles frame 50.

The device 40 further comprises a projector device 1 which substantially corresponds to the projector devices 1 described with regard to FIGS. 1 and 4.

The projector device 1 is attached to the frame 50 via a fastening section 5. As described above, the projector device 1 comprises the alignment device 4. By means of the alignment device 4, the position and the orientation of the projector 2 can be adjusted with respect to the fastening section 5, thus with respect to the frame 50 and as a consequence to the human eye of the patient wearing the device 40.

The alignment device 4 is formed such that the projector 2 can be moved relative to the fastening section 5 in five movement directions 10, 11.

Three movement directions are longitudinal directions 10, 10', 10", wherein optionally each longitudinal direction is oriented substantially orthogonal to the other longitudinal directions.

In this exemplary embodiment, a first longitudinal movement direction 10 corresponds to a longitudinal axis of a human head, a second longitudinal movement direction 10" corresponds to a transversal axis of a human head, and a third movement longitudinal direction 10' corresponds to a sagittal axis of a human head, as will be described in more detail with respect to FIGS. 6 to 8.

The two remaining movement directions are directions of rotation 11, 11'.

In this exemplary embodiment, a first direction of rotation 11' is oriented such that a pantoscopic angle of the projector 2 with respect to the eye 110 can be adjusted, and a second direction of rotation 11 is oriented such that a wrap angle of the projector 2 with respect to the eye 110 can be adjusted, as will be described in more detail with respect to FIGS. 6 to 8.

For providing the movement directions 10, 10', 10", 11, and 11', the alignment device 5 comprises a plurality of kinematic pairs which are shown in generic form, as kinematic pairs are per se known.

The longitudinal movement directions 10, 10', 10" are provided by means of prismatic joints. In detail, one of the prismatic joints is arranged in proximity to the fastening section 5. This prismatic joint provides linear movement in the longitudinal movement direction 10. A second prismatic joint is arranged adjacent to the first prismatic joint and provides movement along the longitudinal movement direction 10'. Adjacent thereto, a first rotating joint is arranged, which provides rotation in the direction of rotation 11. Moreover, a further prismatic joint is provided for enabling movement in longitudinal movement direction 10". In addition, a further rotational joint is provided for providing rotation in direction of rotation 11'.

Furthermore, alignment device 5 comprises a plurality of locking units, wherein each of the locking units (not shown) is allocated to a respective kinematic pair for locking or releasing movement in the respective movement direction. Locking units are per se known, and for instance may be implemented in the form of a locking screw or a surface comprising a high coefficient of friction.

As can be seen in FIG. 5, the main axis 7 of the camera 6 is aligned with a main axis 3 of the projector 2 and hence with the central axis 107 of the light beam 100. According to this exemplary embodiment, the main axis 3 and the main axis 7 are concentrically aligned. With other words, the camera 6 and the projector 2 are arranged in line facing opposite sides of the projector device 2.

Moreover, the device 40 comprises a lens 60 held by the frame 50. The lens 60 according to this embodiment is shaded, here tinted. By providing the tinted lens 60, the eye pupil diameter 112 is naturally enlarged as less ambient light falls into the eye pupil 111. Hence, alignment of the central axis 107 to the center 106 or the viewing axis, respectively, may be facilitated.

Figure 6:
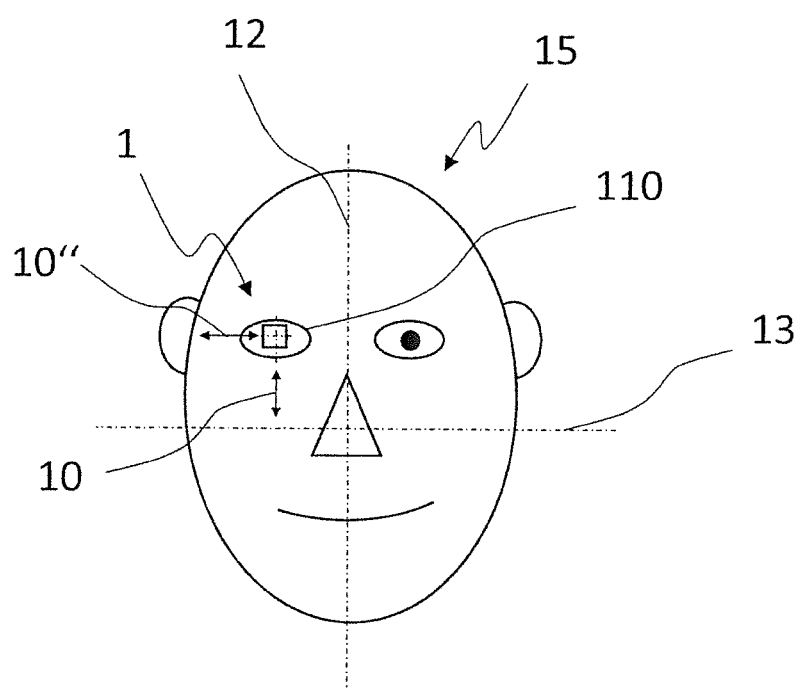
FIG. 6 is a schematic front view of a human head having a projector device for projecting a light beam onto a retina of a human eye placed in front of an eye.

FIG. 6 is a schematic front view of a human head 15 having a projector device 1 for projecting a light beam onto a retina of a human eye placed in front of the eye 110.

The projector device 1 corresponds to the projector device 1 described with respect to FIGS. 1 and 5. For better visibility, the projector device 1 is shown in reduced form and the device 40 is spared.

As can be seen, longitudinal movement direction 10" is oriented substantially parallel to transversal axis 13 of the human head 15. Hence, a transversal or lateral adjustment of the projector 2 and hence the light beam 100 with respect to human eye 110 can be performed.

The longitudinal movement direction 10 corresponds to a longitudinal axis 12 of the human head 15. Hence, by means of longitudinal direction 10, the projector 2 can be lowered or raised with respect to the eye 100.

Figure 7:
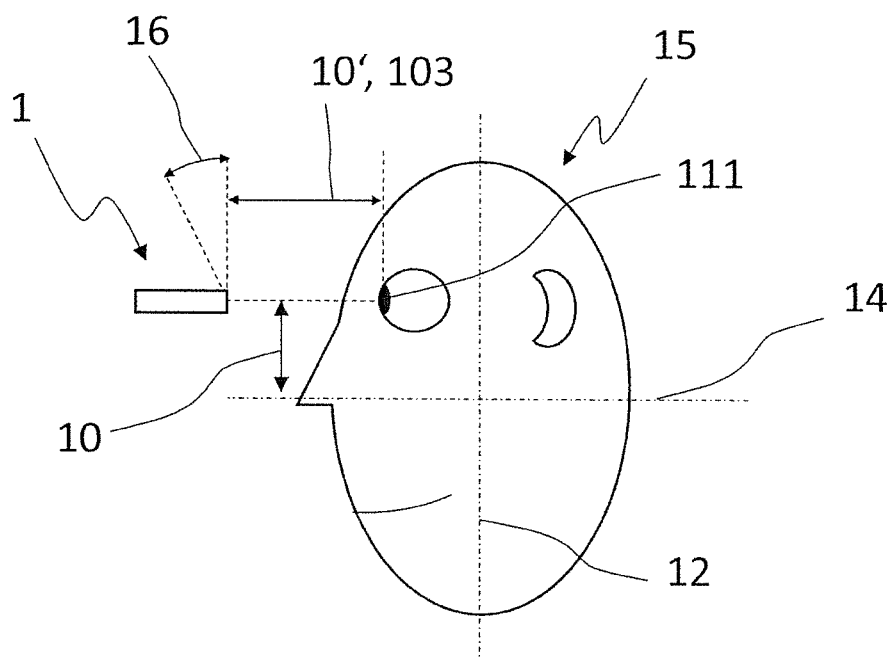
FIG. 7 is a schematic side view of the human head of FIG. 6.

FIG. 7 is a schematic side view of the human head 15 of FIG. 6. As can be seen, longitudinal movement direction 10' essentially corresponds to the sagittal axis 14. Hence, by the longitudinal movement direction 10', the eye relief can be adjusted to correspond to the exit pupil distance 103.

Moreover, via the direction of rotation 11' (see FIG. 5) the pantoscopic angle 16 of the projector 2, hence the light beam 100, with regard to the human eye 110, hence the eye pupil 111, can be adjusted.

Figure 8:
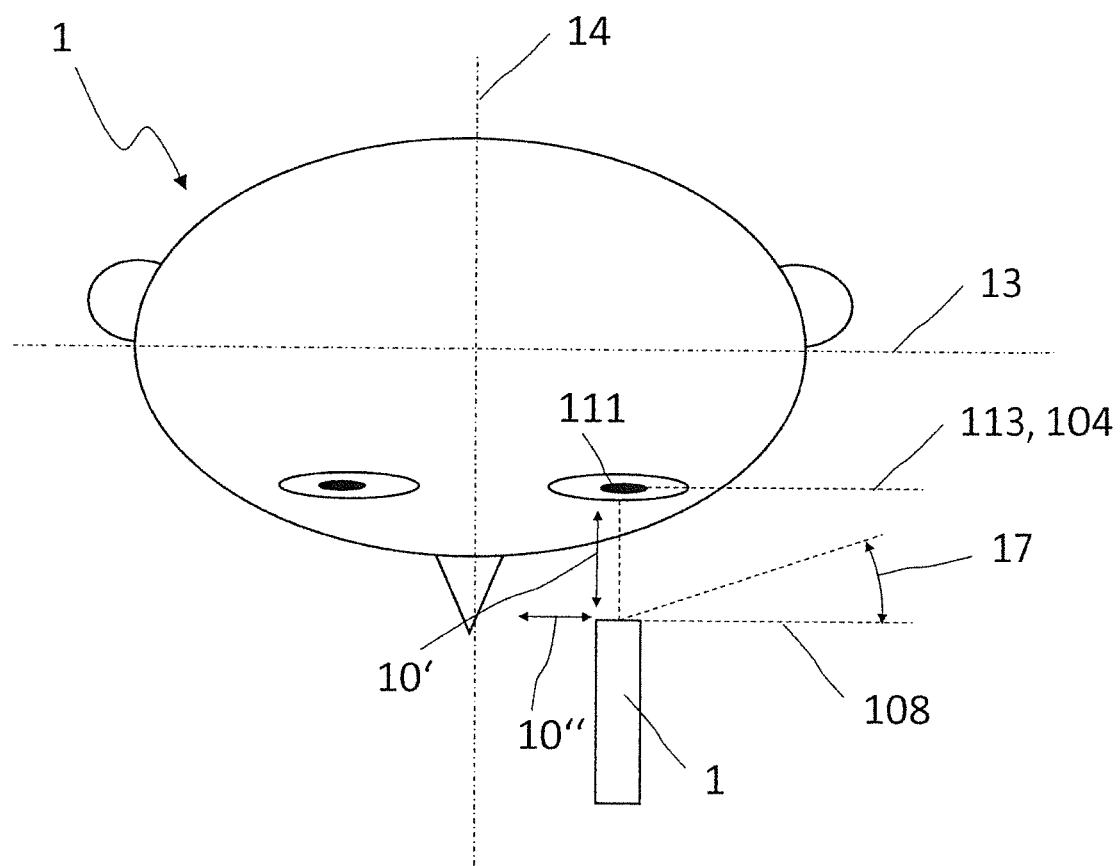
FIG. 8 is a schematic top view of the human head of FIG. 6.

FIG. 8 is a schematic top view of the human head 15 of FIG. 6. As can be additionally seen in this view, by means of direction of rotation 11 (see FIG. 5) the wrap angle 17 of the projector 2, hence the light beam 100, with regard to the human eye 110, hence the eye pupil 111, can be adjusted.

That is, by means of the above-mentioned five movement directions 10, 10', 10", 11, and 11', the light beam 100 can be centered and aligned with regard to the center of the eye pupil 111 and the eye relief can be adjusted such that the exit pupil plane is aligned with the eye pupil plane.

Consequently, the light beam 100 enters the eye 110 in its entirety and moreover is aligned such that it is directed onto the retinal implant 30.

Figure 9:
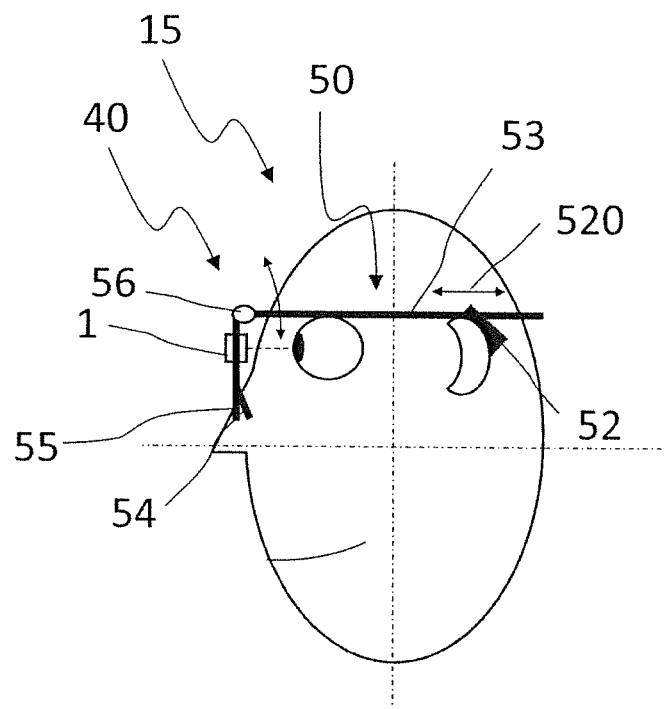
FIG. 9 is a schematic side view of a human head wearing a device according to FIG. 5.

FIG. 9 is a schematic side view of a human head 15 wearing a device 40 according to FIG. 5. The device 40 according to this exemplary embodiment in addition optionally comprises hinges 56 which are arranged between a front frame 55 and temples 53 of the frame 50. By means of hinge 56, a temple 53 is pivotable relative to the front frame 55.

Moreover, on each temple 53, a displaceable ear pad 52 is arranged which can be displaced in the displacement direction 520. For supporting front frame 55 on the patient's nose, adjustable nose pads 54 are provided. By means of the aforementioned parts 52, 54 and 56, the frame 50 can be adjusted to the patient's individual head form prior to adjusting the projector 2 and hence aligning the light beam 100 with respect to the eye pupil 111 of the patient as described above. In particular, the ear pads 52 can be moved forward or backward on the temples 53 relatively to each other to adjust the wrap angle 17 of the front frame 55 and hence of the projector device 1.

Similarly to hinge 56, there can be a further hinge at the location of hinge 56 to tune the angle of the temples 53 relatively to the front frame 55 for a potential adjustment of the wrap angle 17. Alternatively, the hinges 56 are arranged to provide pivoting of the temples 53 relative to the front frame 55 about at least two pivot axes.

Figure 10:
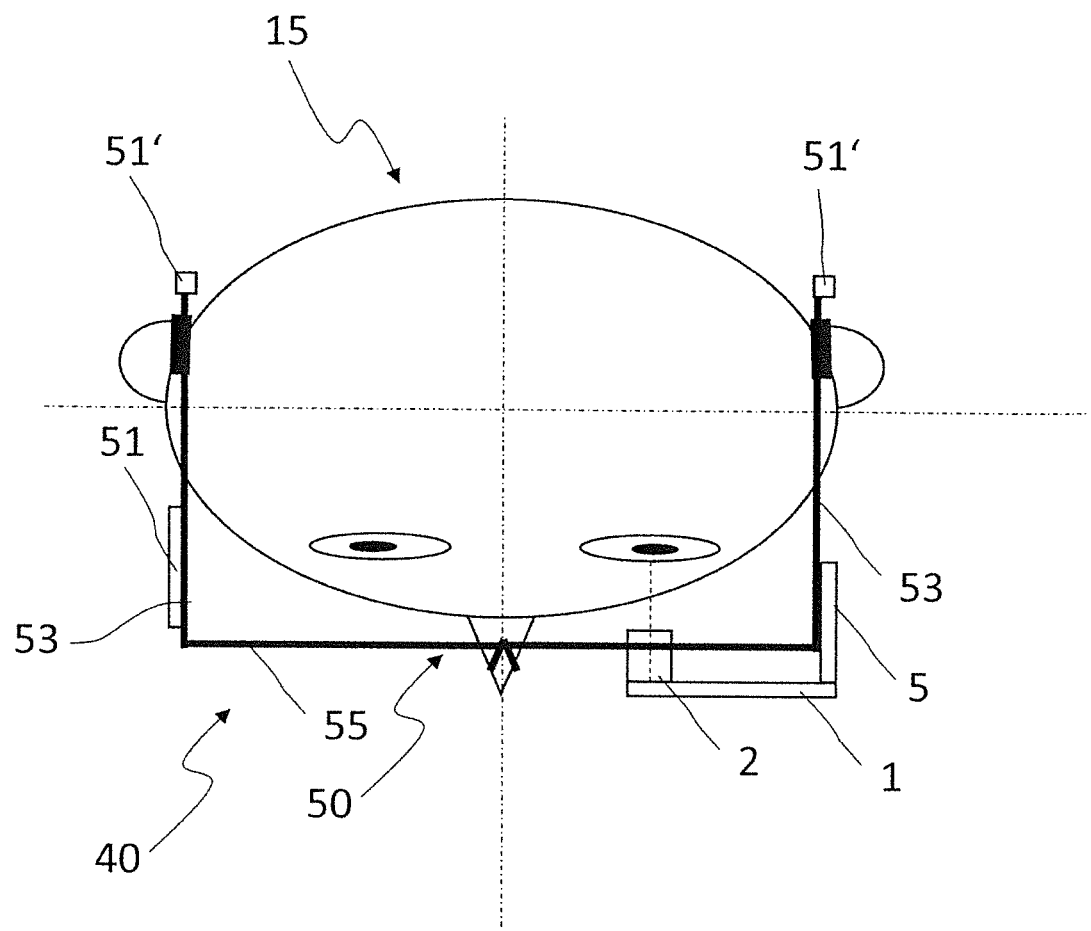
FIG. 10 is a schematic top view of the head of FIG. 9.

FIG. 10 is a schematic top view of the head 15 of FIG. 9. In this view, optional counterweights 51 and 51' are shown. Counterweight 51 is arranged on the side of the frame 50 opposite to the side at which the projector device 1 is arranged such that the lateral weight distribution of the device 40 is balanced. In addition, optional counterweights 51' contribute to a balanced distribution along the sagittal axis 14. Thereby, a wearing comfort of the device 40 may be increased.

Figure 11:
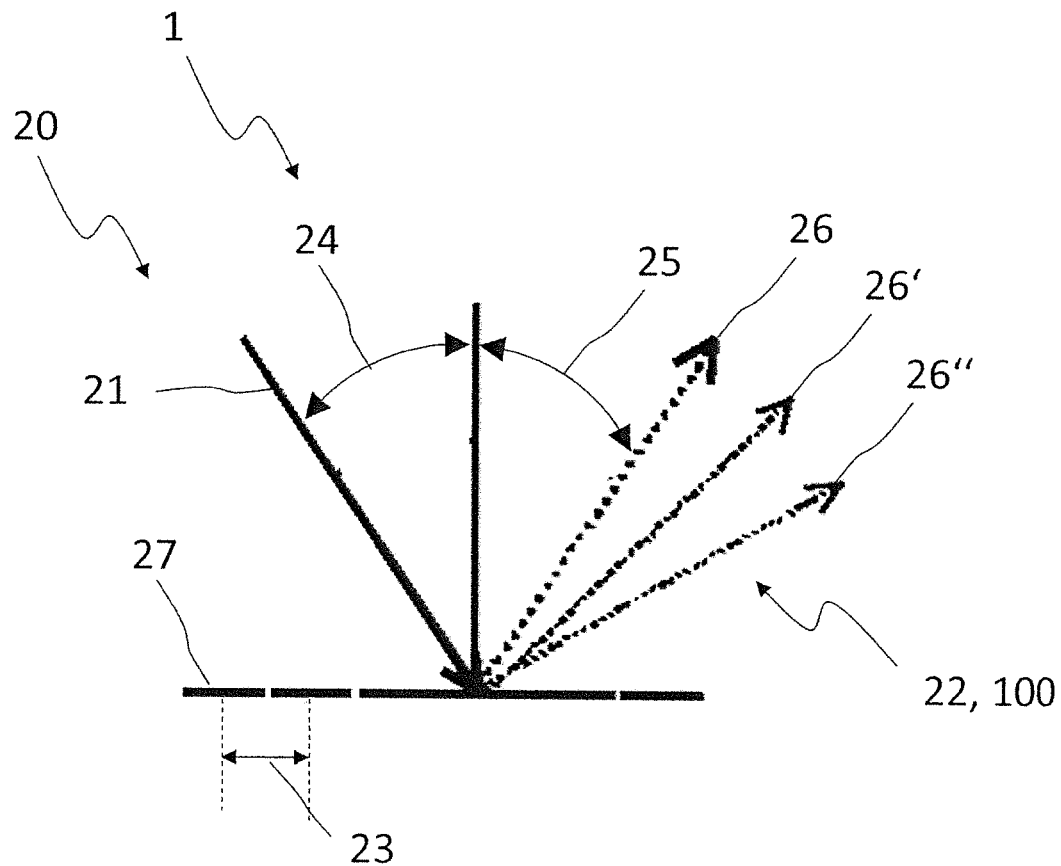
FIG. 11 is a schematic side view of a micromirror array according to a preferred embodiment.
Figure 12:
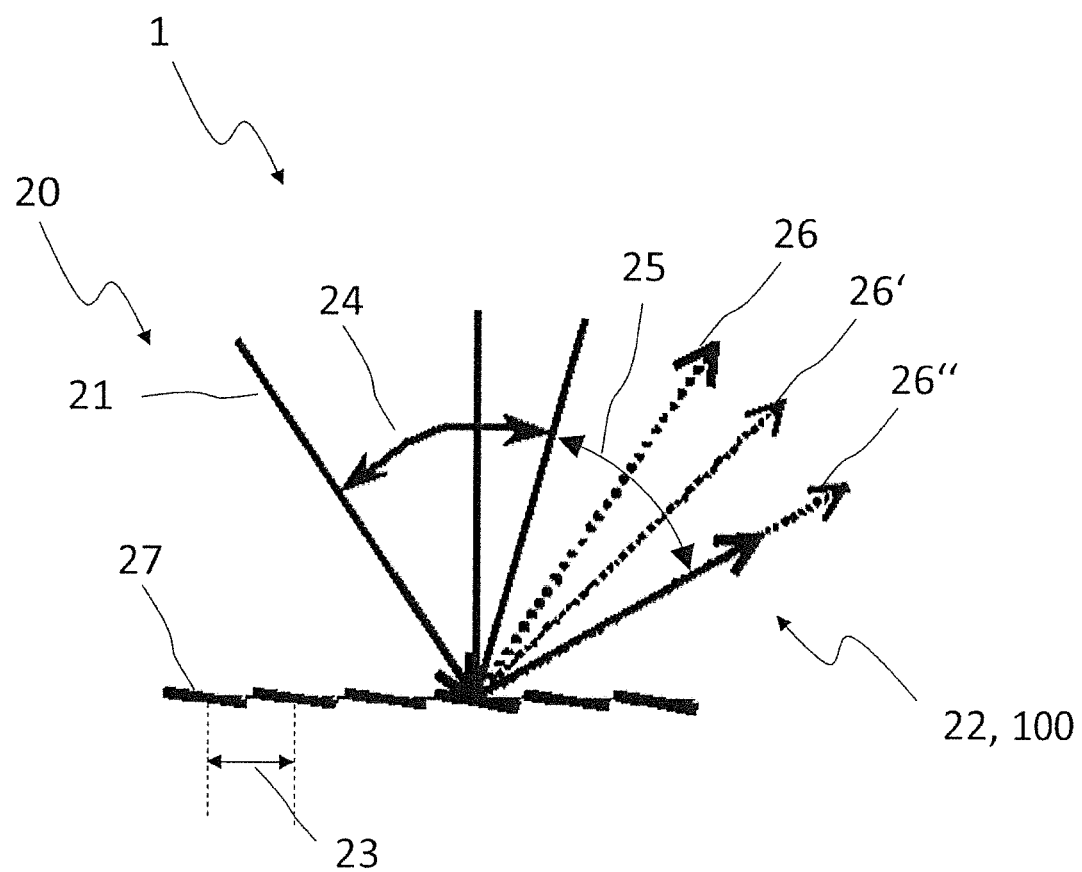
FIG. 12 is a schematic side view of the micromirror array according to FIG. 11 having tilted micromirrors.

FIGS. 11 and 12 show schematic side views of a micromirror array 20 which may be part of a projector device 1 according to a preferred exemplary embodiment.

FIG. 11 is a schematic side view of the micromirror array 20, wherein the light beam 100 is based on patterning of coherent incident light 21 directed onto the micromirror array 20, in this exemplary embodiment NIR light emitted by a laser diode.

Several orders of diffraction, corresponding to light beams in constructive interference, of respective intensity maxima 26, 26', 26" of the reflected output beam 22 appear out of the micromirror array 20 due to the pitch 23 of the micromirrors 27. Energy is distributed mostly in the zeroth order intensity maxima 26. Hence, the incident angle 24 is equal to the output angle 25. Here, substantially the total light energy of the light beam 100 is distributed in the zeroth order 26 only.

FIG. 12 is a schematic side view of the micromirror array 20 having tilted micromirrors 27. Due to the tilting of the micromirrors 27, the light energy of the coherent light 51 is distributed differently in the different orders of intensity maxima 26, 26', 26", such that for example the second order maxima 26' gets most of the energy.

If the incident angle 24 is slightly decreased, the energy will be distributed between the first and second order 26' and 26". Hence, by adjusting the incident angle 24, the energy of the incident coherent light 21 can be distributed in either one or two output beams 22.

Moreover, if the micromirrors 27 are tilted in two dimensions, the energy of the incident light 21 can be split into four output beams 22.

In this regard, the incident angle 24 of the coherent incident light 21 and a pitch 23 of the micromirrors 27 of the micromirror array 20 are configured such that a distance between the intensity maxima 26, 26', 26" of adjacent orders of diffraction, that is of the two most powerful orders of diffraction, of the output beam 22 at the exit pupil plane is equal to or greater than 7 mm, preferably equal to or greater than 8 mm, more preferably equal to or greater than 10 mm.

Alternatively or in addition, the projector device is adapted such that the incident angle 24 of the coherent incident light 21 and the pitch 23 of the micromirrors 27 of the micromirror array 20 are configured such that the majority of the power of the output beam 22 goes into a single order of diffraction, according to this embodiment in intensity maximum 26. Preferably, 80% to 95%, more preferably 90% of the power of the light is directed into this order of diffraction.

Figure 13:
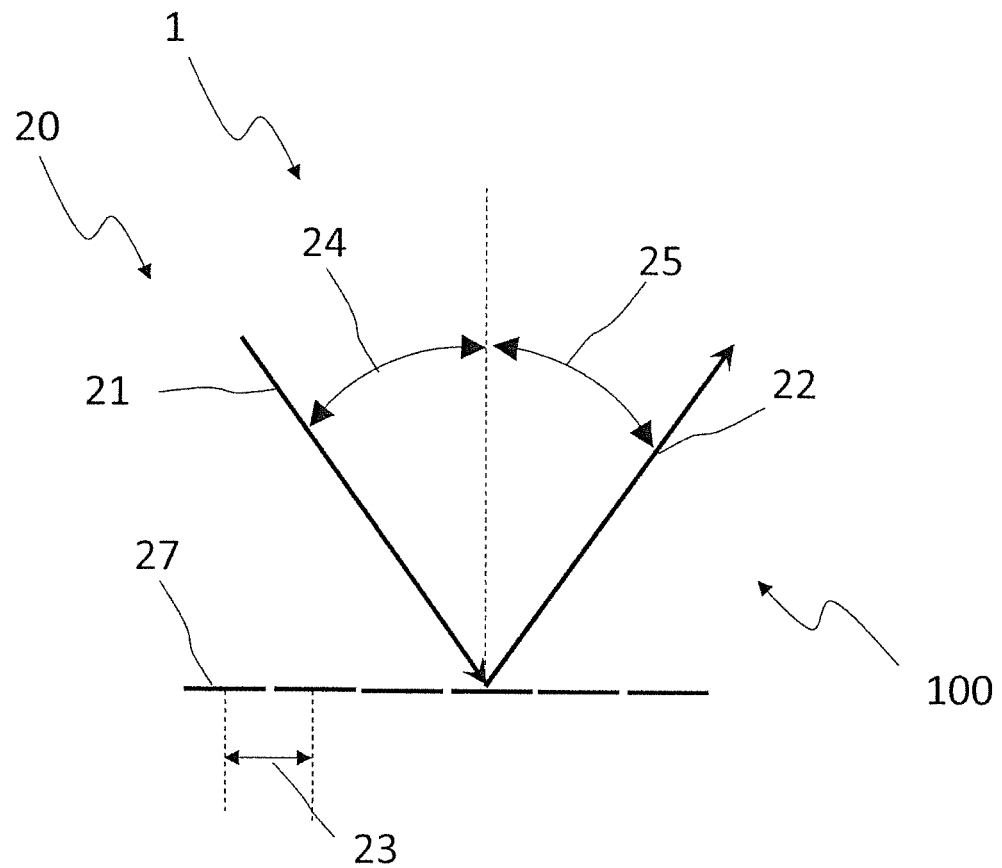
FIG. 13 is a schematic side view of a micromirror array according to another preferred embodiment.

FIG. 13 is a schematic side view of a micromirror array 20 which may be part of a projector device 1 according to another preferred exemplary embodiment, wherein the light beam 100 is based on patterning of incoherent incident light 21 directed onto the micromirror array 20, in this exemplary embodiment NIR light emitted by an LED.

As can be seen, due to the incoherence of the light beam 100, the output beam 22 is based on reflection of the incident light 21 and patterning according to the structure of the micromirror array 20 only. Substantially no diffraction occurs.

It will be obvious for a person skilled in the art that these embodiments and items only depict examples of a plurality of possibilities. Hence, the embodiments shown here should not be understood to form a limitation of these features and configurations. Any possible combination and configuration of the described features can be chosen according to the scope of the invention.

LIST OF REFERENCE NUMERALS 1 projector device
2 projector
3 main axis
4 alignment device
fastening section
6 camera
7 main axis
8 eye observation module
10 longitudinal movement direction
11 direction of rotation
12 longitudinal axis
13 transversal axis
14 sagittal axis
15 head
16 pantoscopic angle
17 wrap angle
20 micromirror array
21 incident light
22 output beam
23 pitch
24 incident angle
25 output angle
26 intensity maximum
27 micromirror
30 retinal implant
40 device for projecting a light beam into a human eye
50 frame
51 counter weight
52 earpad
520 displacement direction
53 temple
54 nose pad
55 front frame
56 hinge
56 pivoting direction
60 lens
100 light beam
101 exit pupil
102 exit pupil diameter
103 exit pupil distance
104 exit pupil plane
105 distance
106 deviation
107 central axis of the light beam
108 projector exit plane
109 output beam diameter
110 eye
111 eye pupil
112 eye pupil diameter
113 eye pupil plane
114 retina
115 iris
116 center of eye pupil

The invention claimed is:

1. A projector device for projecting a light beam onto a retinal area of a human eye, comprising
a projector for projecting a light beam from the exterior of a human eye through a pupil and onto a modified retinal area of the eye, the light beam being a single light beam;
wherein the projector comprises a sensor unit that monitors an eye pupil diameter of the eye onto which the light beam is projected and comprises an adjustment unit that adjusts an exit pupil diameter of the light beam such that the exit pupil diameter of the light beam is set smaller than the eye pupil diameter of the eye; and
wherein the projector comprises an alignment device that aligns a central axis of the light beam with a viewing axis defined by an axis passing through a center of the eye pupil and a center of a retinal implant of the eye.

2. The projector device according to claim 1, further comprising a sensor unit for monitoring an ambient light intensity, wherein the sensor unit comprises a camera and/or a photodetector, wherein the projector comprises an adjustment unit for adjusting the exit pupil diameter based on the monitored value of the ambient light intensity.

3. The projector device according to claim 1, being configured to control an irradiance of the light beam.

4. The projector device according to claim 1, wherein, when the alignment device aligns the central axis of the light beam with a viewing axis, a maximum deviation between the central axis of the light beam and the center of the eye pupil is equal to or less than 1 mm.

5. The projector device according to claim 4, wherein the alignment device is configured for aligning the central axis of the light beam with a viewing axis, being defined as the axis passing by the center of the eye pupil and a center of an implant of the eye, wherein a maximum deviation between the central axis of the light beam and the viewing axis is equal to or less than 1°.

6. The projector device according to claim 1, further comprising a camera for capturing patterns of interest in front of the projector device, wherein a content of the light beam is based on the captured pattern of interest,
wherein a main axis of the camera is aligned with a main axis of the light beam, wherein the camera and the projector are arranged in line facing opposite sides of the projector device.

7. The projector device according to claim 1, wherein the projector device comprises a micromirror array, wherein the light beam is based on patterning of incident light directed onto the micromirror array.

8. The projector device according to claim 7, wherein an incident angle of the coherent light and a pitch of the micromirrors of the micromirror array are configured such that a distance at the exit pupil plane between intensity maxima of adjacent orders of diffraction of an output beam is equal to or greater than 7 mm, equal to or greater than 8 mm, or equal to or greater than 10 mm.

9. The projector device according to claim 8, wherein the incident angle of the coherent light and the pitch of the micromirror array are configured such that a majority of the power of the output beam goes into a single order of diffraction.

10. The projector device according to claim 1, further comprising a shaded lens or a tinted lens.

11. The projector device according to claim 1 further comprising a frame such that the projector device is fixed to the frame.

12. The device according to claim 11, wherein the frame is a spectacles frame, and/or wherein the frame comprises a headband, and/or wherein the frame comprises a headring, and/or the frame comprises ear stoppers.

13. The projection device according to claim 4, wherein the alignment device comprises an eye tracking device embedded in the projection device.

14. The projector device according to claim 7, wherein the micromirror array, is a micromirror device and the light is emitted by a laser, laser diode, and/or an LED.

15. A method for projecting an image onto a retinal area of a human eye, the method comprising:
projecting a light beam from the exterior of a human eye through the pupil and onto a modified retinal area of the eye, the light beam being a single light beam;
a sensor unit monitoring an eye pupil diameter of the eye onto which the light beam is projected;
an adjustment unit adjusting an exit pupil diameter of the light beam such that the exit pupil diameter of the light beam is set smaller than the eye pupil diameter of the eye; and
an alignment device aligning a central axis of the light beam with a viewing axis defined by an axis passing through a center of the eye pupil and a center of a retinal implant of the eye.

16. The method according to claim 15, further comprising aligning a central axis of the light beam to a center of the eye pupil, wherein a maximum deviation between the central axis of the light beam and the center of the eye pupil is equal to or less than 1 mm.

17. The method according to claim 15, wherein a maximum deviation between the central axis of the light beam and the viewing axis is equal to or less than 1°.

18. The method according to claim 16, further comprising
monitoring the eye pupil diameter of the eye the light beam is projected to and/or
monitoring an ambient light intensity, and
adjusting the exit pupil diameter based on the monitored value of the eye pupil diameter and/or the ambient light intensity.

19. The method according to claim 15, wherein the light beam is based on patterning of coherent light directed onto a micromirror array, wherein an incident angle of the coherent light and a pitch of the micromirrors are configured such that a distance at the exit pupil plane between intensity maxima of adjacent orders of diffraction of an output beam is equal to or greater than 7 mm, equal to or greater than 8 mm, or equal to or greater than 10 mm.

20. The method according to claim 16, wherein the light beam is based on patterning of coherent light directed onto a micromirror array, wherein an incident angle of the coherent light and a pitch of the micromirrors are configured such that a majority of the power of the output beam goes into a single order of diffraction.

* * * * *